(12) United States Patent
Zhang et al.

(10) Patent No.: US 11,866,692 B2
(45) Date of Patent: Jan. 9, 2024

(54) FERMENTATION FUNGAL SUBSTANCE OF ASTRAGALUS MEMBRANACEUS PAECILOMYCES CICADAE AND ITS USE

(71) Applicant: BinZhou Medical University, Yantai (CN)

(72) Inventors: Jiayu Zhang, Yantai (CN); Long Dai, Yantai (CN); Shaoping Wang, Yantai (CN); Zikai Geng, Yantai (CN); Yuqi Wang, Yantai (CN)

(73) Assignee: BinZhou Medical University

( * ) Notice: Subject to any disclaimer, the term of this patent is extended or adjusted under 35 U.S.C. 154(b) by 0 days.

(21) Appl. No.: 17/776,529

(22) PCT Filed: Sep. 2, 2020

(86) PCT No.: PCT/CN2020/112945
§ 371 (c)(1),
(2) Date: May 12, 2022

(87) PCT Pub. No.: WO2021/093425
PCT Pub. Date: May 20, 2021

(65) Prior Publication Data
US 2022/0380719 A1   Dec. 1, 2022

(30) Foreign Application Priority Data

Nov. 15, 2019 (CN) .......................... 201911119896.4

(51) Int. Cl.
*C12N 1/14*   (2006.01)
(52) U.S. Cl.
CPC ............ *C12N 1/14* (2013.01); *C12N 2523/00* (2013.01)
(58) Field of Classification Search
CPC .... C12N 1/14; C12N 2523/00; A61K 36/481; A61K 2236/19; A61K 36/06; C12R 2001/07
See application file for complete search history.

(56) References Cited

FOREIGN PATENT DOCUMENTS

| CN | 1663424 A | 9/2005 |
|----|-----------|--------|
| CN | 108315266 A | 7/2018 |
| CN | 109749941 A | 5/2019 |
| CN | 109954006 A | 7/2019 |
| CN | 110711212 A | 1/2020 |

OTHER PUBLICATIONS

Ren X, He L, Cheng J, Chang J. Optimization of the solid-state fermentation and properties of a polysaccharide from Paecilomyces cicadae (Miquel) Samson and its antioxidant activities in vitro. PLoS One. Feb. 3, 2014;9(2):e87578. doi: 10.1371/journal.pone 0087578. PMID: 24498337; PMCID: PMC3911990. (Year: 2014) .*

Zhu et al., Cellulose Chem. Technol., 2016, vol. 50, No. 2, p. 257-263. (Year: 2016).*

Chongyan, Z. et al., "Establishment of Bidirectional Fermentation System of Paecilomyces cicadae/Astragalus Membranaceus and Study on Its Components," World Chinese Medicine, Dec. 2018, pp. 3195-3198, vol. 13, No. 12. [Providing English Translation of Abstract only].

International Search Report for Application No. PCT/CN2020/112945 dated Oct. 28, 2020, 3 pages.

Jia, H. et al., "Estimating the Relationship Between Hypertriglyceridemia and Hyperuricemia," Deciphering Health Codes in Physical Examination, Jul. 2013, p. 174. [Providing English Translation of Abstract only].

Liu, X et al., "Research and Related Literature Analysis on Microbial Fermentation of Astragalus Membranaceus (Chinese Medicinal Herb Huang Qi)," Lishizhen Medicine and Materia Medica Research, Oct. 2015, p. 2470, vol. 26, No. 10.

Lu, T. et al., "The Anti-Hyperuricemic Activity in a Fermented Product of Huang Qi (Astragalus Root) Residues)," Jiangsu Agricultural Sciences, Sep. 2013, p. 288, vol. 41, No. 9.

\* cited by examiner

*Primary Examiner* — Kade Ariani
(74) *Attorney, Agent, or Firm* — Lerner David LLP

(57) ABSTRACT

Provided is a fermentation fungal substance of *Astragalus membranaceus*/*Paecilomyces cicadae* and its use. The fermentation fungal substance is obtained by solid fermentation with *Astragalus membranaceus* powder as a fermentation substrate and *Paecilomyces cicadae* as a fermentation strain. The fermentation fungal substance of *Astragalus membranaceus*/*Paecilomyces cicadae* in the present disclosure plays a significant role in treating hyperuricemia and/or hypertriglyceridemia.

7 Claims, 2 Drawing Sheets

FERMENTATION FUNGAL SUBSTANCE OF ASTRAGALUS MEMBRANACEUS PAECILOMYCES CICADAE AND ITS USE

CROSS-REFERENCE TO RELATED APPLICATION

This application is a U.S. national stage application, filed under 35 U.S.C. § 371, of International Patent Application No. PCT/CN2020/112945, filed on Sep. 2, 2020, which claims priority from Chinese Application No. 201911119896.4, filed Nov. 15, 2019, all of which is incorporated by reference herein in its entirety.

TECHNICAL FIELD OF THE DISCLOSURE

The present disclosure relates to a fermentation fungal substance for traditional Chinese medicine and its use, specifically to a fermentation fungal substance of *Astragalus membranaceus/Paecilomyces cicadae* and its use for manufacturing a medicament for treating hyperuricemia and/or hypertriglyceridemia.

BACKGROUND OF THE DISCLOSURE

As for fermentation of traditional Chinese medicine, a fermentation process of medicinal materials in certain environmental conditions (for example, temperature, humidity, air, moisture, etc.) with the help of enzymes and microorganisms may change their original performance, enhance their effects, provide new effects and increase their numbers of medication, so as to meet the needs of clinical medication. The conventional fermentation of traditional Chinese medicine is a microbial fermentation technology, in which after purified or treated, the medicine is foamed to produce a yellow and white mildew coat through a catalytic decomposition of microorganisms and enzymes under certain temperature and humidity conditions. Geographical environments and seasonal variation may have an effect on species and quantities of strains involved in a fermentation process of traditional Chinese medicine, and the fermentation process may be mostly judged and controlled by subjective experience of a human being. Thus, it is difficult to guarantee safety, effectiveness, stability and controllability of fermented traditional Chinese medicine.

The fermentation process of traditional Chinese medicine has gradually changed from conventional natural fermentation to modern fermentation. In the modern fermentation, the fermentation process can be monitored in real time, which is more targeted and more conducive to an exhaustive study of fermentation mechanism of traditional Chinese medicine. A novel fermentation technology is performed by using Chinese medicinal materials as a medium and using some fungi for solid state or liquid state fermentation. Various enzymes and metabolites produced from fungi in the fermentation may result in a change of chemical components of medicinal materials and their content, which have a function of "modifying" medicinal materials. Moreover, such a novel bidirectional fermentation has many advantages, such as cheap and easy-access equipment, wide sources of raw materials, simple experimental operation, simple fermentation methods, high economic benefit, and short production cycle and so on. Consequently, large-scale industrialized production may be realized in practice.

*Astragalus membranaceus* is a commonly used traditional Chinese medicine, which has some effects, such as tonifying Qi and lifting yang, strengthening exterior and reducing sweat, inducing diuresis to alleviate edema, and so on. Some studies relate to modern fermentation of *Astragalus membranaceus*. LU Tan et al. reported that a fermentation product was obtained with *Ganoderma lucidum* as fermentation strain and *Astragalus* residue as medium, and it had anti-hyperuricemia activity (Anti-hyperuricemia activity of a fermentation product of *Astragalus* residue, Jiangsu Agricultural Science [J], Vol. 41, No. 9, 2013, pp. 288-291). ZHAO Chongyan et al. established a bidirectional fermentation system of *Astragalus membranaceus/Paecilomyces cicadae*, and found that the content of polysaccharides and total saponins decreased, but the content of flavonoids increased in the medicinal fungal substance of *Astragalus membranaceus* after fermentation (Establishment of bidirectional fermentation system of *Astragalus membranaceus/Paecilomyces cicadae* and study on its components, World Chinese Medicine, December 2018, Vol. 13, No. 12, pp. 3195-3198).

However, there is no report on pharmacological activity of a fermentation fungal substance of *Astragalus membranaceus/Paecilomyces cicadae*.

SUMMARY OF THE DISCLOSURE

An objective of the present disclosure is to provide a fermentation fungal substance of *Astragalus membranaceus/Paecilomyces cicadae* and its novel use for manufacturing a medicament.

The objective of the present disclosure is realized by the following technical solution.

The present disclosure provides a use of fermentation fungal substance of *Astragalus membranaceus/Paecilomyces cicadae* for manufacturing a medicament for treating hyperuricemia and/or hypertriglyceridemia, wherein the fermentation fungal substance of *Astragalus membranaceus/Paecilomyces cicadae* is obtained by solid fermentation with *Astragalus membranaceus* powder as a fermentation substrate and *Paecilomyces cicadae* as a fermentation strain.

In the present disclosure, preferably, the fermentation fungal substance of *Astragalus membranaceus/Paecilomyces cicadae* is used for manufacturing a medicament for treating hyperuricemia complicated by hypertriglyceridemia.

In the present disclosure, preferably, the fermentation fungal substance of *Astragalus membranaceus/Paecilomyces cicadae* is obtained by the following method:

(1) mixing *Astragalus membranaceus* powder with water, and then subjecting to a sterilization operation to obtain a solid medium of *Astragalus membranaceus*;

(2) inoculating *Paecilomyces cicadae* into the solid medium of *Astragalus membranaceus*, and culturing at a culture temperature of 24-30° C. and a relative humidity of 50-90% for 7-30 days, so as to obtain the fermentation fungal substance of *Astragalus membranaceus/Paecilomyces cicadae*.

In the present disclosure, preferably, in step (1), the *Astragalus membranaceus* powder has a particle size of 6-20 mesh, more preferably 8-14 mesh, still more preferably 8 mesh. Adopting the particle size of the *Astragalus membranaceus* powder may be conducive to growth of *Paecilomyces cicadae*.

In the present disclosure, preferably, in step (1), a weight ratio of the *Astragalus membranaceus* powder to water is 1-5:1, more preferably 1.5-3:1, still more preferably 2-2.5:1. Adopting the above ratios may be helpful for the inoculated *Paecilomyces cicadae* to fully contact with the *Astragalus membranaceus* powder, resulting in a better fermentation effect. Furthermore, the solid medium of *Astragalus membranaceus* obtained while the weight ratio of the *Astragalus membranaceus* powder to water is 2-2.5:1 is more suitable for growth of *Paecilomyces cicadae*, resulting in a higher growth rate of *Paecilomyces cicadae* and a higher yield of *Astragalus membranaceus/Paecilomyces cicadae* fermentation bacteria.

In step (1), the sterilization operation may adopt conventional sterilization conditions, without special restrictions. According to an embodiment of the present disclosure, the sterilization operation is performed in a high-pressure steam sterilization pot at 90° C. for 60 minutes.

In the present disclosure, preferably, in step (2), *Paecilomyces cicadae* is obtained by activating and culturing a *Paecilomyces cicadae* strain. The *Paecilomyces cicadae* strain is known, preferably a strain with the number of cfcc81169 stored in the China Forestry Culture Collection Center. The activation culture method may adopt a conventional method in the art, without any restriction. According to an embodiment of the present disclosure, said activating and culturing a *Paecilomyces cicadae* strain comprises the following steps: inoculating the *Paecilomyces cicadae* strain on potato glucose agar (PDA) slant culture medium, placing it in a box with a constant temperature of 27° C. and a constant relative humidity of 80% for activation culture for 5 days, so as to obtain activated *Paecilomyces cicadae*; and then picking out the activated *Paecilomyces cicadae* with an inoculation loop and placing it in a potato glucose liquid medium; culturing the medium in a shaking table at 25° C. and 140 r·min$^{-1}$ for 7 days to obtain *Paecilomyces cicadae* and a seed solution of *Paecilomyces cicadae*. The seed solution may be directly used to be inoculated into the solid medium of *Astragalus membranaceus*.

In the present disclosure, preferably, in step (2), *Paecilomyces cicadae* has an inoculation amount of 5-20 wt %, more preferably 8-15 wt %, still more preferably 8-12 wt %, based on the weight of the *Astragalus membranaceus* powder. Selecting the above inoculation amount may be conducive to achieving a higher growth rate of *Paecilomyces cicadae* and a higher yield of fermentation fungal substance of *Astragalus membranaceus/Paecilomyces cicadae*, and saving the amount of *Paecilomyces cicadae*.

In the present disclosure, preferably, in step (2), the culture temperature is 25-29° C., more preferably 26-28° C. The relative humidity is 60-90%, more preferably 70-90%. The culture time is preferably 14-24 days, more preferably 20-24 days. According to a preferred embodiment of the present disclosure, the culture temperature is 26-28° C., the relative humidity is 70-90%, and the culture time is 20-24 days. Better fermentation effects can be achieved in the above culture conditions. The culture can be carried out in an incubator with a constant temperature and a constant humidity.

In the present disclosure, preferably, in step (2), the seed solution is also inoculated into the solid medium of *Astragalus membranaceus*.

The present disclosure also provides the fermentation fungal substance of *Astragalus membranaceus/Paecilomyces cicadae* prepared by the abovementioned preparation method. The content of polysaccharides in the fermented fungal substance of *Astragalus membranaceus/Paecilomyces cicadae* is significantly higher than that of *Astragalus membranaceus*.

Compared with *Astragalus membranaceus*, the polysaccharide content in the fermented fungal substance of the *Astragalus membranaceus/Paecilomyces cicadae* of the present disclosure is significantly increased. The fermentation fungal substance of *Astragalus membranaceus/Paecilomyces cicadae* of the present disclosure plays a significant role in treating hyperuricemia and/or hypertriglyceridemia.

Figure 1:
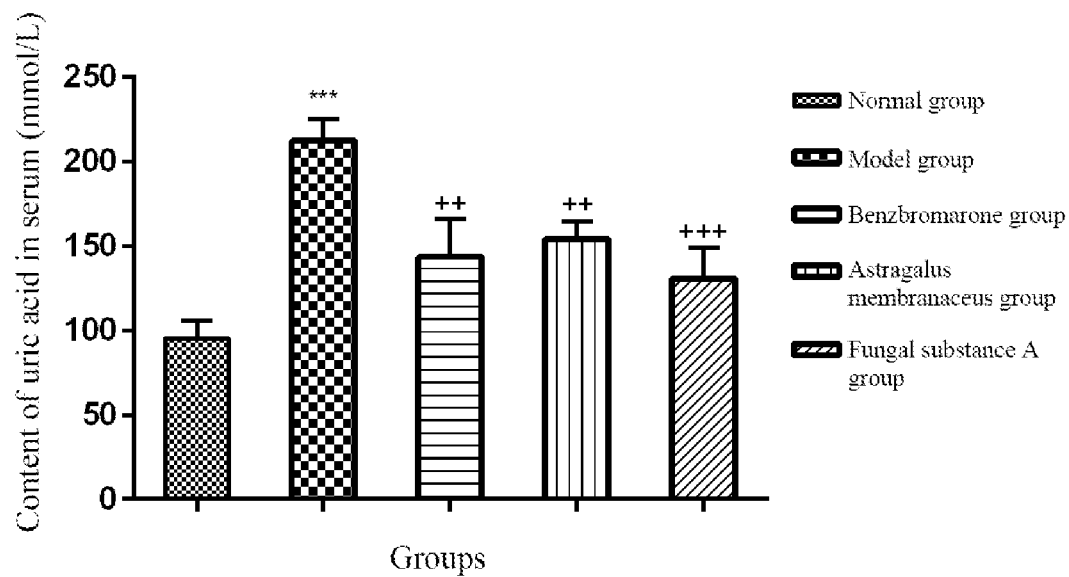
FIG. 1 shows the comparison of serum UA levels in rats with hyperuricemia.

Note: compared with the normal group, * indicates a very significant difference (P<0.001),  indicates a significant difference (P<0.01). Compared with the model group, +++ indicates a very significant difference (P<0.001), ++ indicates a significant difference (P<0.01), + indicates a statistical difference (P<0.05).

DETAIL DESCRIPTION OF THE DISCLOSURE

The present disclosure provides a novel use of fermentation fungal substance of *Astragalus membranaceus/Paecilomyces cicadae* for manufacturing a medicament. The embodiments of the present disclosure are described in detail below.

The embodiments of the disclosure are further described below through specific examples.

In the following examples, a *Paecilomyces cicadae* strain was provided by the China Forestry Culture Collection Center, with the number of cfcc81169. The *Paecilomyces cicadae* strain was inoculated on potato glucose agar (PDA) slant culture medium and activated in a box with a constant temperature of 27° C. and a constant relative humidity of 80% for 5 days, so as to obtain activated *Paecilomyces cicadae*. The activated *Paecilomyces cicadae* was picked out with an inoculation loop and placed in potato glucose liquid medium. It was cultured in a shaking table at 25° C. and 140 r·min$^{-1}$ for 7 days to obtain *Paecilomyces cicadae* and a seed solution of *Paecilomyces cicadae*.

Reagents: Potassium oxonate was purchased from Sigma, U.S.; Benzbromarone tablet (Narcarin) was purchased from Excella GmbH, Germany. A calibrating solution, a quality control liquid and a test kit were purchased from Beijing Leadman Biochemical Technology Co., Ltd. The batch No. of triglyceride test kit is 112293k. The batch No. of uric acid test kit is 00275. The batch No. of urea nitrogen test kit is 01049. The batch No. of creatinine test kit is 04210.

Animal: Sprague Dawley (SD) rats, male, with a body mass of 220-250 g, were purchased from Beijing Vital River Laboratory Animal Technology Co., Ltd. with the license number of SCXK (Beijing) 2016-0006.

Instruments: A CX-4 Pro automatic biochemical analyzer is a product from Beckman Company, U.S.; a R200D electronic analytical balance (1/100000) is a product from Sartorius Company, Germany; a Millipore Synergy UV water ultrapuring machine is a product from Millipore, U.S.; a BXM-30R high pressure steam sterilizer is a product from Xi'an Yichuang Instrument Equipment Co., Ltd; a UV-2000 UV-Vis spectrophotometer is a product from Beijing Ruili Analytical Instrument Co., Ltd; a FW-100 high-speed pulverizer is a product from Tianjin Taisite Instrument Co., Ltd; a LHS-80HC-II incubator with constant temperature and humidity is a product from Shanghai Bluepard Instruments Co., Ltd.

The fermentation and culture in examples 1-2, comparative examples 1-3 are carried out in parallel, with exactly the same *Astragalus membranaceus* and its amount, and the same culture process and operations.

Example 1

*Astragalus membranaceus* was crushed and sieved through 8 mesh to obtain *Astragalus membranaceus* powder. The *Astragalus membranaceus* powder was mixed evenly with distilled water with a weight ratio of 2.5:1, sterilized in a steam sterilization pot at 90° C. for 60 min, and then cooled to room temperature to obtain a solid medium of *Astragalus membranaceus*. *Paecilomyces cicadae* was evenly inoculated into the solid medium of *Astragalus membranaceus* with an inoculation amount of 10 wt % of *Astragalus membranaceus*. The inoculated medium was cultured at a constant temperature of 26° C. and a constant relative humidity of 80% for 24 days to obtain fermentation fungal substance of *Astragalus membranaceus/Paecilomyces cicadae* A (hereinafter referred to as "fungal substance A").

Example 2

*Astragalus membranaceus* was crushed and sieved through 8 mesh to obtain *Astragalus membranaceus* powder. The *Astragalus membranaceus* powder was mixed evenly with distilled water with a weight ratio of 2.5:1, sterilized in a steam sterilization pot at 90° C. for 60 min, and then cooled to room temperature to obtain a solid medium of *Astragalus membranaceus*. *Paecilomyces cicadae* was evenly inoculated into the solid medium of *Astragalus membranaceus* with an inoculation amount of 10 wt % of *Astragalus membranaceus*; and the seed solution of *Paecilomyces cicadae* was evenly inoculated into the solid medium of *Astragalus membranaceus* with an inoculation amount of 4 wt % of the *Astragalus membranaceus* powder. The inoculated medium was cultured at a constant temperature of 26° C. and a constant relative humidity of 80% for 24 days to obtain fermentation fungal substance of *Astragalus membranaceus/Paecilomyces cicadae* B (hereinafter referred to as "fungal substance B").

Comparative Example 1

*Astragalus membranaceus* was crushed and sieved through 8 mesh to obtain *Astragalus membranaceus* powder. The *Astragalus membranaceus* powder was mixed evenly with distilled water with a weight ratio of 1:1.5, sterilized in a steam sterilization pot at 90° C. for 60 min, and then cooled to room temperature to obtain a solid medium of *Astragalus membranaceus*. *Paecilomyces cicadae* was evenly inoculated into the solid medium of *Astragalus membranaceus* with an inoculation amount of 10 wt % of *Astragalus membranaceus*. The inoculated medium was cultured at a constant temperature of 26° C. and a constant relative humidity of 80% for 24 days to obtain fermentation fungal substance of *Astragalus membranaceus/Paecilomyces cicadae* C (hereinafter referred to as "fungal substance C").

Comparative Example 2

*Astragalus membranaceus* was crushed and sieved through 8 mesh to obtain *Astragalus membranaceus* powder. The *Astragalus membranaceus* powder was mixed evenly with distilled water with a weight ratio of 2.5:1, sterilized in a steam sterilization pot at 90° C. for 60 min, and then cooled to room temperature to obtain a solid medium of *Astragalus membranaceus*. *Paecilomyces cicadae* was evenly inoculated into the solid medium of *Astragalus membranaceus* with an inoculation amount of 4 wt % of *Astragalus membranaceus*. The inoculated medium was cultured at a constant temperature of 26° C. and a constant relative humidity of 80% for 24 days to obtain fermentation fungal substance of *Astragalus membranaceus/Paecilomyces cicadae* D (hereinafter referred to as "fungal substance D").

Comparative Example 3

*Astragalus membranaceus* was crushed and sieved through 8 mesh to obtain *Astragalus membranaceus* powder. The *Astragalus membranaceus* powder was mixed evenly with distilled water with a weight ratio of 2.5:1, sterilized in a steam sterilization pot at 90° C. for 60 min, and then cooled to room temperature to obtain a solid medium of *Astragalus membranaceus*. *Paecilomyces cicadae* was evenly inoculated into the solid medium of *Astragalus membranaceus* with an inoculation amount of 20 wt % of *Astragalus membranaceus*. The inoculated medium was cultured at a constant temperature of 26° C. and a constant relative humidity of 80% for 24 days to obtain fermentation fungal substance of *Astragalus membranaceus/Paecilomyces cicadae* E (hereinafter referred to as "fungal substance E").

Comparative Example 4

*Astragalus membranaceus* was crushed and sieved through 8 mesh to obtain *Astragalus membranaceus* powder.

Experimental Example 1

Determination of Consumption Rate for Fungal Growth

Samples of the fermentation fungal substance of *Astragalus membranaceus/Paecilomyces cicadae* A-E were taken on the 24th day of fermentation. The bottom and surface of the fermentation substrate were covered with dense mycelium. The wet weight of mycelium was measured. The mycelium was washed with distilled water for 3 times, then dried in an oven at 60° C. to a constant weight. The weight was measured. The weight change after fermentation was calculated, and the consumption rate was calculated. The consumption rate was higher, while the culture conditions were more suitable for mycelial growth.

Consumption rate=(weight of medicinal materials−weight of fermented fungal substance after drying)/weight of medicinal materials×100%.

The results are shown in Table 1.

TABLE 1

| Group | Consumption rates (%) |
| --- | --- |
| Fungal substance A | 20.74 |
| Fungal substance B | 23.39 |
| Fungal substance C | 17.78 |
| Fungal substance D | 15.32 |
| Fungal substance E | 21.02 |

Experimental Example 2

Determination of Active Component Content

Total polysaccharides were extracted from the fungal substance A of Example 1 and the *Astragalus membranaceus* powder of Comparative example 4, respectively. The content of the total polysaccharides was determined by a colorimetry with sulfuric acid/phenol (the method was the same as that described in the following literature: YANG Li et al., Comparison of the Methods for Determination of *Astragalus* Polysaccharides in Radix Astragali, Chinese Journal of Pharmaceuticals [J], 2005, 36 (9): 562-563).

Total flavonoids were extracted from the fungal substance A of Example 1 and the *Astragalus membranaceus* powder of Comparative example 4 with ethyl acetate. The content of the total flavonoids was determined by a colorimetry with $NaNO_2/Al(NO_3)_3$ (the method was the same as that described in the following literature: FANG Shubiao, etc., Quantitative determination of total flavonoids in *Astragalus* Mongholicus by UV spectrophotometry, Chinese Remedies and Clinics [J], 2007, 7 (12): 899-901).

For the above measurements, three samples were taken in parallel, the content was determined, and the average value was calculated.

The results are shown in Table 2.

TABLE 2

| Group | Content of total polysaccharides (mg/g) | Content of total flavonoids (mg/g) |
|---|---|---|
| *Astragalus membranaceus* powder | 23.72 ± 0.48 | 0.89 ± 0.01 |
| Fungal substance A | 31.35 ± 0.76*** | 0.46 ± 0.01*** |

Note:
***indicates that there is a very significant difference comparing with the *Astragalus membranaceus* powder group ($P < 0.001$)

Compared with the *Astragalus membranaceus* powder group, the content of total polysaccharides in the fungal substance A increased significantly, which was 1.32 times that of the *Astragalus membranaceus* powder group; the content of flavonoids decreased significantly, which was only ½ of that of the *Astragalus membranaceus* powder group. A change of *Astragalus* polysaccharides component may be an important reason for an efficacy change in the fermentation fungal substance of *Astragalus membranaceus/Paecilomyces cicadae* in comparison with *Astragalus membranaceus* materials.

Experimental Example 3

Efficacy Test

1. Modeling and Administration

SD rats were randomly divided into normal group, hyperuricemia (HUA) model group, positive medicine control group, *Astragalus membranaceus* group and fungal substance A group based on body mass, with 8 rats in each group. They were used in experiments after one week of adaptive feeding in an animal room.

All groups were fed with normal feed. In addition, the normal group was treated with distilled water by gavage. Other groups were treated with 300 mg·kg$^{-1}$ of potassium oxonate by gavage each day for modeling. After 1 hour, the positive medicine control group was treated with 20 mg·kg$^{-1}$ of benzbromarone by gavage, the *Astragalus membranaceus* group was treated with 300 mg·kg$^{-1}$ of an *Astragalus membranaceus* powder solution by gavage, and the fungal substance A group was treated with 300 mg·kg$^{-1}$ of a fungal substance A solution by gavage. The treatment was performed twice each day for 14 consecutive days, and the dosage was 10 mL·kg$^{-1}$.

2. Collection of Serum Samples

Four hours after administration on the last day, blood samples were taken from the orbital venous plexus of the rats. The blood samples were stored at 4° C. overnight, and then centrifuged to obtain serum, which was for determination of biochemical indexes.

3. Determination of Biochemical Indexes

After routine calibration and quality control, the contents of uric acid (UA), urea nitrogen (BUN), creatinine (CRE) and triglyceride (TG) in serum were determined by an automatic biochemical analyzer.

4. Data Analysis

All test results are expressed in the form of "mean±standard deviation". Excel and software SPSS17.0 were utilized for calculation and statistics. After all data were tested for normal distribution and homogeneity of variance, single factor analysis of variance was performed. The difference between the two groups was tested by t-test. When $P<0.05$, the difference was considered to be statistically significant.

5. Results 5.1 Effects on Serum UA Level in Rats with Hyperuricemia

As shown in FIG. 1, compared with the normal group, rats in the hyperuricemia model group induced by potassium oxonate had a very significantly higher serum UA level ($P<0.001$). It is suggested that the hyperuricemia model of rats was successfully established. Compared with the model group, the serum UA levels of rats in the positive benzbromarone group and the *Astragalus membranaceus* group were significantly reduced, and the serum UA level of rats in the fungal substance A group was very significantly reduced. It is indicated that the fungal substance A group had a stronger effect on reducing uric acid than the *Astragalus membranaceus* group.

5.2 Effects on Serum BUN Level in Rats with Hyperuricemia

Figure 2:
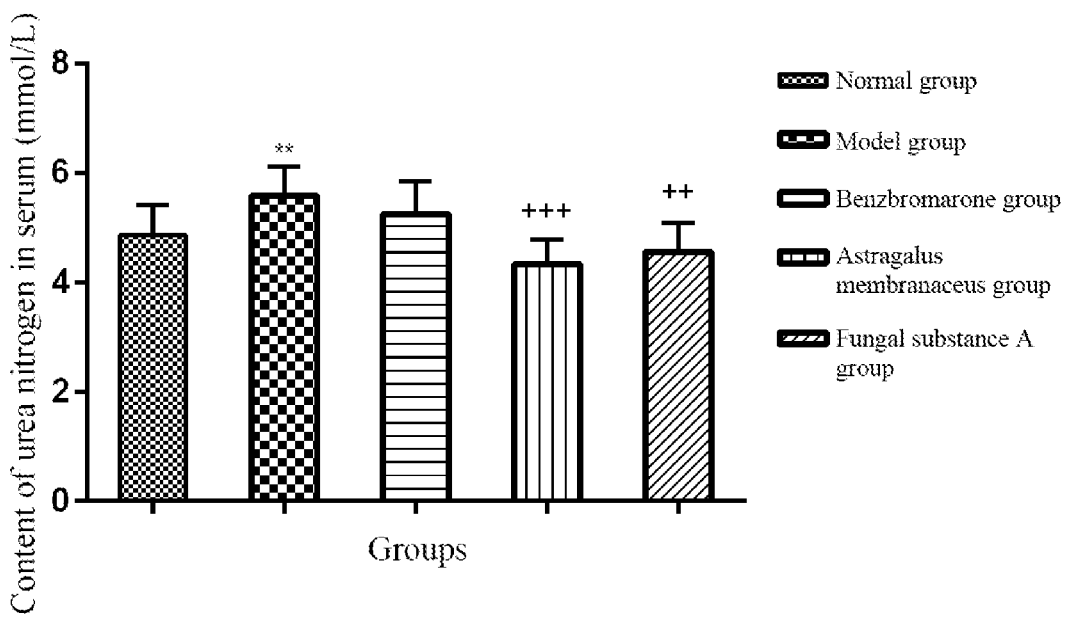
FIG. 2 shows the comparison of serum BUN levels in rats with hyperuricemia.

As shown in FIG. 2, compared with the normal group, rats in the hyperuricemia model group induced by potassium oxonate had a significantly higher serum BUN level ($P<0.01$). Compared with the model group, the serum BUN level of rats in the fungal substance A group was significantly reduced, and the serum BUN level of rats in the *Astragalus membranaceus* group was very significantly reduced.

5.3 Effects on Serum CRE Level in Rats with Hyperuricemia

Figure 3:
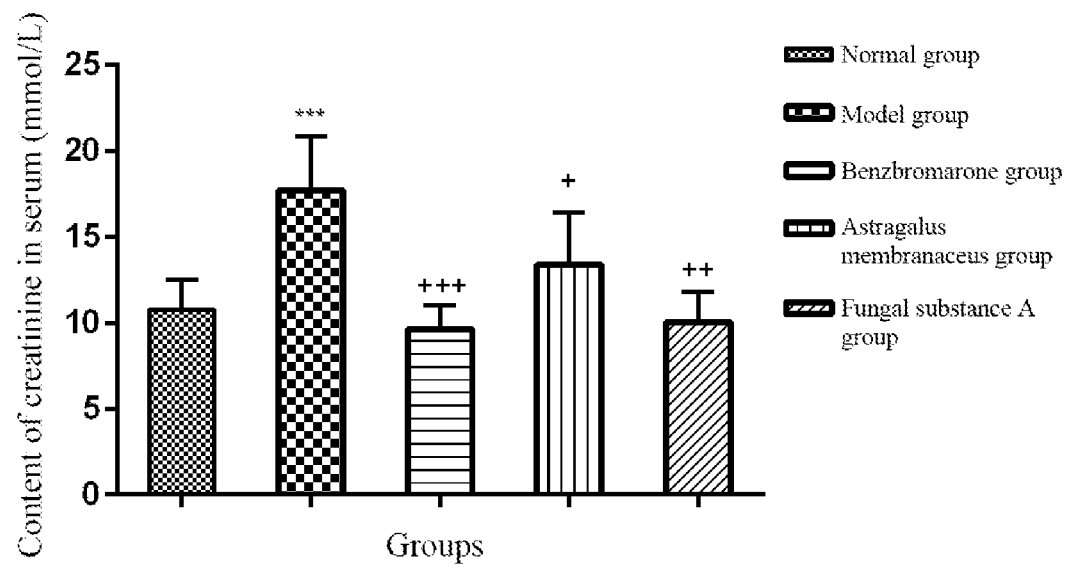
FIG. 3 shows the comparison of serum CRE levels in rats with hyperuricemia.

As shown in FIG. 3, compared with the normal group, rats in the hyperuricemia model group induced by potassium oxonate had a very significantly higher serum CRE level ($P<0.001$). Compared with the model group, the serum CRE level of rats in the positive benzbromarone group was very significantly reduced, and the serum CRE level of rats in the fungal substance A group was significantly reduced. The fungal substance A group had a stronger effect on reducing serum CRE than the *Astragalus membranaceus* group.

5.4 Effects on TG Level in Rats with Hyperuricemia

Figure 4:
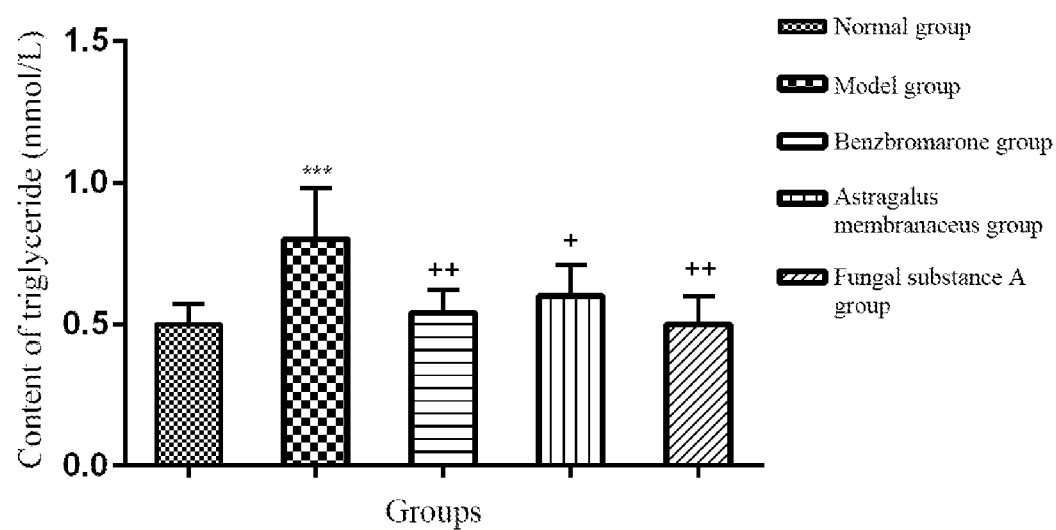
FIG. 4 shows the comparison of TG levels in rats with hyperuricemia.

Hyperuricemia is usually complicated by hypertriglyceridemia. As shown in FIG. 4, compared with the normal group, rats in the hyperuricemia model group induced by potassium oxonate had a very significantly higher serum TG level (P<0.001). Compared with the model group, the serum TG levels of rats in the positive benzbromarone group and the fungal substance A group were significantly reduced, and the serum TG level of rats in the *Astragalus membranaceus* group was apparently reduced. It is indicated that the fungal substance A group had better effects than the *Astragalus membranaceus* group.

The present disclosure is not limited to the embodiments described above. Any modification, improvement, and replacement which do not depart from the essence of the present disclosure and which those skilled in the art are able to think of fall within the scope of the present disclosure.

What is claimed is:

1. A method for preparing a fungal fermentation substance of *Astragalus membranaceus/Paecilomyces cicadae* comprising:
   (1) mixing an *Astragalus membranaceus* powder with water, and then subjecting to a sterilization operation to obtain a solid medium of *Astragalus membranaceus*; wherein a weight ratio of the *Astragalus membranaceus* powder to water is 1.5-3:1;
   (2) inoculating an *Paecilomyces cicadae* into the solid medium of *Astragalus membranaceus*, and culturing at a culture temperature of 26-28° C. and a relative humidity of 70-90% for 20-24 days, so as to obtain the fungal fermentation substance of *Astragalus membranaceus/Paecilomyces cicadae*;
      wherein the *Paecilomyces cicadae* has an inoculation amount of 5-20 wt %, based on the weight of the *Astragalus membranaceus* powder;
   (3) obtaining the fungal fermentation substance of *Astragalus membranaceus/Paecilomyces cicadae* by solid fermentation with the *Astragalus membranaceus* powder as a fermentation substrate and the *Paecilomyces cicadae* as a fermentation strain;
      wherein the *Astragalus membranaceus* powder has a particle size of 8-14 mesh for conducive growth of *Paecilomyces cicadae* and in step (1) the weight ratio of the *Astragalus membranaceus* powder to water is for inoculated *Paecilomyces cicadae* to fully contact with the *Astragalus membranaceus* powder resulting in a better fermentation effect;
      wherein a polysaccharide content in the fungal fermentation substance of the *Astragalus membranaceus/Paecilomyces cicadae* is significantly increased as compared to *Astragalus membranaceus*.

2. The method according to claim 1, wherein in step (1), the weight ratio of the *Astragalus membranaceus* powder to water is 2-2.5:1.

3. The method according to claim 1, wherein in step (2), the *Paecilomyces cicadae* is obtained by activating and culturing a *Paecilomyces cicadae* strain.

4. The method according to claim 3, wherein in step (2), said activating and culturing a *Paecilomyces cicadae* strain comprises the following steps: inoculating the *Paecilomyces cicadae* strain on potato glucose agar slant culture medium, placing it in a box with a constant temperature of 27° C. and a constant relative humidity of 80% for activation culture for 5 days, so as to obtain activated *Paecilomyces cicadae*; and then picking out the activated *Paecilomyces cicadae* with an inoculation loop and placing it into the potato glucose liquid medium, culturing the medium in a shaking table at 25° C. and 140 r·min$^{-1}$ for 7 days to obtain the *Paecilomyces cicadae* and a seed solution of *Paecilomyces cicadae*.

5. The method according to claim 4, wherein in step (2), the *Paecilomyces cicadae* has an inoculation amount of 8-15 wt %, based on the weight of the *Astragalus membranaceus* powder.

6. The method according to claim 5, wherein in step (2), the seed solution is inoculated into the solid medium of *Astragalus membranaceus*.

7. A fungal fermentation substance of *Astragalus membranaceus/Paecilomyces cicadae* obtained by the method according to claim 1.

* * * * *